United States Patent [19]

Heefner et al.

[11] Patent Number: 5,457,051
[45] Date of Patent: Oct. 10, 1995

[54] ENANTIOSELECTIVE HYDROLYSIS OF KETOPROFEN ESTERS BY BEAUVERIA BASSIANA AND ENZYMES DERIVED THEREFROM

[75] Inventors: Donald L. Heefner, Hudson; Charles M. Zepp, Berlin, both of Mass.

[73] Assignee: Sepracor, Inc., Marlborough, Mass.

[21] Appl. No.: 28,320

[22] Filed: Mar. 9, 1993

[51] Int. Cl.$^6$ ..................................................... C12P 41/00
[52] U.S. Cl. ........................... 435/280; 435/911; 435/171
[58] Field of Search ................................... 435/171, 280, 435/911, 196, 197

[56] References Cited

U.S. PATENT DOCUMENTS

| | | | |
|---|---|---|---|
| 4,436,813 | 3/1984 | Wood et al. | 435/109 |
| 4,650,755 | 3/1987 | Wood et al. | 435/43 |
| 4,762,793 | 8/1988 | Cesti et al. | 435/280 |
| 4,857,462 | 8/1989 | Maier et al. | 435/197 |
| 4,886,750 | 12/1989 | Bertola et al. | 435/136 |
| 4,987,077 | 1/1991 | Charnley et al. | 435/223 |
| 5,037,751 | 12/1991 | Bertola et al. | 435/197 |
| 5,057,427 | 10/1991 | Wald et al. | 435/280 |
| 5,075,233 | 12/1991 | Bertola et al. | 435/280 |
| 5,077,217 | 12/1991 | Matson et al. | 435/280 |
| 5,108,916 | 4/1992 | Cobbs et al. | 435/134 |
| 5,108,917 | 4/1992 | Bertola et al. | 435/136 |
| 5,180,671 | 1/1993 | Nishizawa et al. | 435/136 |

FOREIGN PATENT DOCUMENTS

| | | |
|---|---|---|
| 227078 | 12/1986 | European Pat. Off. . |
| 330217 | 8/1989 | European Pat. Off. . |
| 461043 | 6/1991 | European Pat. Off. . |
| WO90/15146 | 6/1990 | WIPO . |
| WO91/13163 | 9/1991 | WIPO . |

OTHER PUBLICATIONS

Wu et al. "Enhancing the Enantioselectivity of Candida Lipase Catalyzed Ester Hydrolysis via Noncovalent Enzyme Modification" *J. Am. Chem. Soc.* 112 1990–1995 (1990).

Iriuchijima and Keiyu "Asymmetric Hydrolysis of (±)-α-Substituted Carboxylic Acid Esters with Microorganisms" *Agric. Biol. Chem.* 45 1389–1392 (1981).

Gu et al. "A Facile Enzymatic Resolution Process For the Preparation of (+)-S-2-(6-Methoxy-2-Naphthyl) Propionic Acid (Naproxen)" *Tetrahedron Letters* 27 1763–1766 (1986).

*Primary Examiner*—John W. Rollins
*Assistant Examiner*—S. Saucier
*Attorney, Agent, or Firm*—Heslin & Rothenberg

[57] ABSTRACT

A process for producing substantially pure R-ketoprofen by the enantioselective hydrolysis of racemic ketoprofen choline ester is disclosed. The process utilizes either intact *Beauveria bassiana* hyphae or an R-specific ester hydrolase isolated therefrom. The ester hydrolase has an approximate molecular weight of 17,800 daltons and an N-terminal sequence of Ala-Pro-Asp-W-Ile-Ile-Gln-Gly-Leu-Ser-Arg-Ala-X-Asp-Gly-Gln-Asp.

14 Claims, No Drawings

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: protein
        ( A ) DESCRIPTION: ester hydrolase ( i i i ) HYPOTHETICAL: no ( v ) FRAGMENT TYPE: N- terminal fragment ( v i ) ORIGINAL SOURCE:
        ( A ) ORGANISM: Beauveria bassiana
        ( B ) STRAIN: ATCC 44860

-continued (x i) SEQUENCE DESCRIPTION: SEQ ID NO: 1:

Ala Pro Asp Xaa Ile Ile Gln Gly Leu Ser Arg Ala Xaa
                  5                     10

Asp Gly Gln Asp
     15

(2) INFORMATION FOR SEQ ID NO:2:

(i) SEQUENCE CHARACTERISTICS:
    (A) LENGTH: 18 amino acids
    (B) TYPE: amino acid
    (D) TOPOLOGY: linear (i i) MOLECULE TYPE: protein
    (A) DESCRIPTION: ester hydrolase (i i i) HYPOTHETICAL: no (v) FRAGMENT TYPE: internal fragment (v i) ORIGINAL SOURCE:
    (A) ORGANISM: Beauveria bassiana
    (B) STRAIN: ATCC 44860

(x i) SEQUENCE DESCRIPTION: SEQ ID NO: 2:

Phe Ala Ile Asn Asn Gln Leu Thr Ala Pro Thr Ala Xaa
                  5                     10

Thr Tyr Val Val Lys
     15

(2) INFORMATION FOR SEQ ID NO:3:

(i) SEQUENCE CHARACTERISTICS:
    (A) LENGTH: 19 amino acids
    (B) TYPE: amino acid
    (D) TOPOLOGY: linear (i i) MOLECULE TYPE: protein
    (A) DESCRIPTION: ester hydrolase (i i i) HYPOTHETICAL: no (v) FRAGMENT TYPE: internal fragment (v i) ORIGINAL SOURCE:
    (A) ORGANISM: Beauveria bassiana
    (B) STRAIN: ATCC 44860

(x i) SEQUENCE DESCRIPTION: SEQ ID NO: 3:

Leu Ile Ala Tyr Pro Ala Tyr Asn Asp Glu Xaa Ala Ala
                  5                     10

Gly Asn Val Pro Asp Lys
     15

ENANTIOSELECTIVE HYDROLYSIS OF KETOPROFEN ESTERS BY BEAUVERIA BASSIANA AND ENZYMES DERIVED THEREFROM

BACKGROUND OF THE INVENTION

Ketoprofen is an α-methylarylacetic acid analgesic/antiinflammatory currently available as the racemic mixture. Because the S-enantiomer has been believed to possess advantages over the R-enantiomer as an analgesic, and because S-α-methylarylacetic acid analgesic/antiinflammatory agents are generally believed superior to their R counterparts, there is extensive literature on the enantioselective production of S-ketoprofen. We have recently discovered that R-ketoprofen enjoys some previously unappreciated advantages as an analgesic and antipyretic. A process for the enantiospecific production of R-ketoprofen on a commercial scale is therefore of considerable utility and interest.

The enantioselective hydrolysis of racemic ketoprofen esters to produce S-ketoprofen is known in the art. Iriuchijima and Keiyu in an early paper [*Agric. Biol. Chem.* 45, 1389–1392 (1981)] disclosed the modestly selective hydrolysis of racemic ketoprofen methyl ester to S-ketoprofen with 38% enantiomeric excess (e.e) in unspecified, low yield using *Mycobacterium smegmatis*. Sih (European application 227078) disclosed the still modestly selective hydrolysis of racemic ketoprofen methyl ester to S-ketoprofen with 60% ee in unspecified yield using *Candida cylindracea* ester hydrolase. Cobbs et al. (U.S. Pat. No. 5,108,916 and PCT application WO90/15146) subsequently disclosed the more selective hydrolysis of alkyl, haloalkyl and glyceryl esters of racemic ketoprofen by ester hydrolases from *Candida rugosa* (formerly called *Candida cylindracea*) to yield S-ketoprofen in very high enantiomeric excess at 20 to 30% conversion. This was accomplished by purifying and separating the ester hydrolase isozymes from *C. rugosa*.

The enantioselective hydrolysis of racemic ketoprofen esters to produce R-ketoprofen has also been reported, albeit in low yield or low ee. Iriuchijima and Keiyu (op. cit.) reported that the methyl ester of ketoprofen was "hydrolyzed a little" by *Aspergillis sojae* to give an undisclosed ee of R-ketoprofen. Goswami (PCT application WO91/13163) disclosed the hydrolysis of racemic ketoprofen methyl ester to R-ketoprofen with 74% ee in 8% conversion by dog liver acetone powder. This is far too inefficient to provide a commercially useful process for R-ketoprofen, even if dog liver were an inexpensive reagent. Cobbs PCT application WO90/15146 appears to disclose the hydrolysis of racemic ethylene glycol ester of ketoprofen to R-ketoprofen in 42 to 64% ee by pig liver esterase and by *Mucor miehei* ester hydrolase.

Wu et al. [*J. Am. Chem. Soc.* 112, 1990-1995 (1990)] have defined a useful measure for enantioselective reactions which combines both the ee and the extent of conversion. It is termed the enantiomeric ratio E, and is defined as:

$$E = \frac{\ln[1-c)(1-ee_s)]}{\ln[1-c)(1+ee_s)]}$$

where $$c = \frac{ee_s}{ee_s + ee_p}$$

$ee_s$ is the enantiomeric excess of substrate (in this case the racemic ester)

$ee_p$ is the enantiomeric excess of product (in this case the R-acid)

The enantiomeric excess is well known in the art and is defined for a resolution of ab→a+b as $$ee_a = \left( \frac{\text{conc. of } a - \text{conc. of } b}{\text{conc. of } a + \text{conc. of } b} \right) \times 100$$

The enantiomeric excess is related to the older term "optical purity" in that both are measures of the same phenomenon. The value of ee will be a number from 0 to 100, zero being racemic and 100 being pure, single enantiomer. A compound which in the past might have been called 98% optically pure is now more precisely described as 96% ee. Processes that yield products of ee less than about 80% are not generally regarded as commercially attractive. Similarly, for commercial processes a goal is to maximize the E value; E values less than 10 are undesirable. The process of Goswami to provide R-ketoprofen has a low enantiospecificity, a very low conversion, and an E value of less than 7 calculated by this method.

There is a need for a commercially useful process for R-ketoprofen. In one approach this devolves to a need for a process for the enantioselective hydrolysis of a racemic ketoprofen ester to produce R-ketoprofen by a process having an E value greater than 10.

Producing R-ketoprofen by selective hydrolysis gives rise to a second consideration: the ester from which to produce R-ketoprofen. The alkyl esters of ketoprofen are insoluble in water and are generally poor substrates for commercial enzymatic hydrolysis because multiphasic/heterogeneous reaction systems suffer from a number of drawbacks on the industrial scale. For example, scale-up and reliability problems are frequently associated with the processing of dispersions and emulsions, and continuous operation and pH control (especially in hydrolytic reactions) are difficult to achieve. Additionally, the phases must be separated before product can be recovered, and excessive interphase mass transfer resistances are often encountered. These are associated with diffusion of the poorly soluble substrate in the aqueous phase. Many of these disadvantages associated with the enzymatic resolution of water insoluble esters of chiral carboxylic esters in heterogeneous reaction systems could be minimized or eliminated if the water-solubility of the ester derivative could be substantially increased.

One approach, as shown for example in the Cobb PCT application, is the addition of surfactants to the solution broth. This appears to provide little advantage. A second approach is the use of water soluble esters. An example of this approach can be found in Dodds et al. European application 461043 which describes a preparation of the choline ester of ketoprofen and its transesterification to R-ketoprofen ethyl ester in very low ee by a protease. (Examples 18 and 20 in the Dodds application report that the transesterfication products had rotations of −0.166° and −0.203° respectively; pure R-ketoprofen ethyl ester has a rotation of −45.5° under the conditions reported.)

Because the primary object of the present invention is to provide a commercially useful process for R-ketoprofen, there is a need for a highly efficient synthesis of a water soluble ester that can be enantioselectively hydrolyzed. There is then a need for an enantioselective hydrolysis of that ester.

SUMMARY OF THE INVENTION

It is an object of the present invention to provide a commercially useful process for R-ketoprofen.

It is a further object to provide a process for the enantioselective hydrolysis of a racemic ketoprofen ester, which process has an E value, as described above, greater than 10. It is a further object to provide an enantioselective synthesis of R-ketoprofen from racemic ketoprofen via the choline ester.

These and other objects, features and advantages are realized in the present invention which, in one aspect, relates to a process for preferentially hydrolyzing R-ketoprofen choline ester in the presence of S-ketoprofen choline ester comprising contacting an aqueous solution of a mixture of ketoprofen choline ester enantiomers with an organism of the species *Beauveria bassiana* at pH 4.0 to pH 8.0 and at a temperature of 10° to 40° C. Preferably the *Beauveria bassiana* is selected from strains ATCC 44860, 38657 and 7159, most preferably strain ATCC 44860. The temperature is preferably about 25° C. and the pH is preferably maintained at 5.5 to 6.5. The aqueous solution may additionally contain a source of nutrients for the *Beauveria bassiana*.

In another aspect, the invention relates to a process for producing R-ketoprofen comprising exposing a choline ester of R-ketoprofen to an organism of the species *Beauveria bassiana*, preferably at pH 5.5 to 6.5 and at about 25° C. The *Beauveria bassiana* may be selected from strains 44860, 38657 and 7159.

In a further aspect, the invention relates to a process for obtaining R-ketoprofen from racemic ketoprofen comprising:

(a) reacting racemic ketoprofen with a suitable precursor to produce a choline ester of racemic ketoprofen;

(b) treating the choline ester of racemic ketoprofen in water with a fungus of the species *Beauveria bassiana* to produce preferentially R-ketoprofen in the presence of S-enriched ketoprofen choline ester; and (c) isolating the R-ketoprofen from the racemic ketoprofen choline ester and S-ketoprofen choline ester.

In a preferred embodiment, racemic ketoprofen is reacted with an activating agent, such as thionyl chloride, to provide an activated ketoprofen, which is then reacted with choline to produce the racemic choline ester. In another embodiment the racemic ketoprofen is reacted with N,N-dimethylethanolamine which is then quaternized to the choline ester with a methylating agent. In another preferred embodiment, an ester hydrolase from a fungus of the species *Beauveria bassiana* is used in place of the fungus itself.

In a further aspect, the same process can be used to obtain S-enriched ketoprofen from racemic ketoprofen by:

(a) reacting racemic ketoprofen with an activating agent to provide an activated ketoprofen;

(b) reacting the activated ketoprofen with choline to provide a choline ester of racemic ketoprofen;

(c) treating the choline ester of racemic ketoprofen in water with a fungus of the species *Beauveria bassiana* to produce a mixture consisting essentially of S-enriched ketoprofen choline ester and R-ketoprofen;

(d) separating the R-ketoprofen from the S-enriched ketoprofen choline ester; and (e) hydrolyzing the S-enriched ketoprofen choline ester. By S-enriched, it is meant that the ester or acid is not a racemate (i.e., a 50:50 mixture of enantiomers) but, rather, that there is an excess of the S-enantiomer (i. e., ee$_{S\text{-}ketoprofen}$>0).

In a further aspect the invention relates to a process for preferentially hydrolyzing R-ketoprofen choline ester in the presence of S-ketoprofen choline ester comprising contacting an aqueous solution of said R-ketoprofen choline ester with a *Beauveria bassiana* ester hydrolase at pH 4.0 to pH 8.0 and at a temperature of 10° to 40° C. A Beauveria ester hydrolase has an approximate molecular weight of 17,800 daltons, or a multiple thereof, exclusive of tryptophan and cysteine, an N-terminal sequence of Ala-Pro-Asp-W-Ile-Ile-Gln-Gly-Leu-Ser-Arg-Ala-X-Asp-Gly-Gln-Asp-(SEQ ID NO:1) and internal sequences of -Phe-Ala-Ile-Asn-Asn-Gln-Leu-Thr-Ala-Pro-Thr-Ala-Y-Thr-Tyr-Val-Val-Lys-(SEQ ID NO:2) and -Leu-Ile-Ala-Tyr-Pro-Ala-Tyr-Asn-Asp-Glu-Z-Ala-Ala-Gly-Asn-Val-Pro-Asp-Lys-(SEQ ID NO:3), where W, X, Y and Z represent unidentified aminoacids.

The terms "contacting with" and "exposing to" indicate that the substrate and the Beauveria ester hydrolase can be brought together not only as traditional reactants in solution, but also by percolation through columns or circulation over membranes as described below or, indeed, by any means that allow the reaction between substrate and water be enhanced through the participation of Beauveria ester hydrolase.

In a further aspect the invention relates to an ester hydrolase having an activity greater than 100 units per milligram of protein produced by the process of:

(a) extracting a plurality of fractured cells of *Beauveria bassiana* with an aqueous buffer at pH 6.5;

(b) filtering or centrifuging the buffer to recover impure ester hydrolase in an aqueous filtrate or supernatant; and (c) contacting the supernatant with a weakly basic anion exchange resin, such as a diethylaminoethyl (DEAE) resin, to produce an aqueous solution of ester hydrolase. The ester hydrolase has an activity of greater than 100 units per milligram of protein in the solution and is capable of hydrolyzing racemic ketoprofen choline ester to R-ketoprofen in greater than 90% ee.

One unit of the enzyme activity is defined as that amount of the enzyme that catalyzes hydrolysis of one nmol of ketoprofen nitrophenyl ester per hour. The ester hydrolase may have the structural elements discussed above and may exist as an oligomer of which the 17,800 dalton monomer is a subunit.

DETAILED DESCRIPTION OF THE INVENTION

The invention relates to processes for selectively hydrolyzing racemic ketoprofen esters to R-ketoprofen. From more than 300 strains of microorganisms 78 were selected by a large-scale screening program for their ability to hydrolyze racemic ketoprofen methyl ester to ketoprofen of indeterminate chirality. The methyl ester was chosen for initial screening because of its ready availability and its suitability for initial screening in which the conversion of an insoluble material (ester) to a soluble material (acid) is advantageous. It is not the optimal ester for a commercial process, as will be discussed below.

A particularly rapid and efficient method of selecting a microorganism capable of transforming a sparingly water-soluble ester (such as ketoprofen methyl ester) into an appreciably more water soluble acid salt (such as a ketoprofen salt) takes advantage of the change in solubility brought about by the transformation. Thus, a suspension of the ester in an aqueous medium, such as agarose, is exposed to a colony or colonies of a microorganism, and the initially opaque medium is observed for signs of translucence or transparence in the vicinity of a colony. Colonies producing transparency in the aqueous medium containing the sparingly soluble precursor are then selected for larger scale incubation using standard microbiological techniques.

The procedure for selecting the microorganism follows the sequence of:

(a) growing a plurality of colonies of microorganisms in an aqueous medium on a substrate. The preferred medium is Brain-Heart Infusion (BHI) and the preferred substrate is agar coated on a plate;

(b) overlaying the colonies with an opaque aqueous medium, preferably agarose buffered to pH 7.0 with phosphate buffer, containing the ester in suspension. The organisms are allowed to continue to grow under the ester layer; and (c) making an initial selection of those colonies over which the opaque medium has become transparent. This constitutes the primary selection.

The 78 selected strains were then grown to stationary phase in liquid medium and subsequently incubated with racemic ketoprofen methyl ester for 48 hours in BHI medium, at 25° C. At the end of this period samples were taken and analyzed by chiral HPLC (Chiracel OJ column, Daicel Chemical Industries, Japan). From the 78 strains, two were selected that appeared promising for R-ketoprofen. Pseudomonas sp. 14696 and *Beauveria bassiana* ATCC 44860 preferentially hydrolyzed the R-methyl ester. The % ee R-acid obtained with Beauveria was 78.8%, while Pseudomonas sp. ATCC 14696 was more selective (at 40% conversion of ester to acid, the R-acid formed had an ee value of 85%). Optically enriched S-acid can also be recovered from this reaction by first isolating the enriched S-ester and subsequently hydrolyzing the S-ester to the S-acid.

Because the solubility of alkyl esters gives rise to the drawbacks discussed above, the choline ester was examined. Initially a synthesis of the choline ester was adapted from the application of Dodds (above). This synthesis proceeded in the conventional manner by reaction of the acid to form the acid chloride; reactions with N,N-dimethylethanolamine to form the tertiary amine ester; and then quaternization with dimethyl sulfate, methyl iodide or methyl chloride to produce the choline methylsulfate, iodide or chloride. An improved synthesis is described as follows:

A 250 mL 3-neck round bottom flask was placed in an appropriate heating mantle and fitted with a 25 mL Dean-Stark trap with condensor and stirrer. The flask was charged with 25.4 gm (0.1 mol) of racemic ketoprofen, 7.5 mL of 97% thionyl chloride (0.1 mol), 2 drops of dimethylformamide and 50 mL of toluene. The Dean-Stark trap was also filled to capacity with toluene. The reaction was heated to reflux and stirred at moderate speed. After 1 hour of reflux 14.5 gm of choline chloride (0.11 mol) was added in 1 dose as a solid and the reaction was allowed to continue at reflux. The choline chloride appeared to remain as a solid until consumed in the reaction. Approximately 20 min. after the addition of choline chloride, the reaction started to foam vigorously; at this point the stir speed was reduced to a minimum and the heat was decreased to just below reflux temperature. A second phase appeared as an oil (ester product) and was insoluble in the toluene. The reaction was allowed to stir at low temperature. After fourteen hours, a sample of the ester layer was dissolved in water and analyzed by C-18 HPLC. The analysis of the ester showed 92% ester and 8% acid. Subsequent experiments increased the yield of ester to >98% by scrupulously drying the choline before use.

In the foregoing example the activating agent was thionyl chloride and the activated ketoprofen was the acid chloride. Other activating agents well-known in the chemical art may be employed in place of thionyl chloride. Thus, for example, O-acyl isoureas can be made from carbodiimides and azides can be made from hydrazides, etc.

Since the physical properties of choline esters are different from those of methyl esters, extrapolation of results from one to the other seemed unwise. Therefore, the most selective organisms from the earlier screening against the methyl ester were re-examined for hydrolytic selectivity against the choline ester. *Beauveria bassiana* exhibited highly specific hydrolytic activity toward the R-choline ester. None of the other organisms were as selective.

The hydrolysis of the methylsulfate and the iodide salts of ketoprofen choline ester by *Beauveria bassiana* were examined. To a 30 mL stationary phase culture of *Beauveria bassiana* ATCC 44860 (BHI medium, pH 7.0) at 25° C., was added 1 g of racemic choline ester of either the methylsulfate or iodide salt and incubation was continued with shaking. At the indicated times samples were taken and analyzed for R-acid and S-ester. The results are shown in Table 1.

TABLE 1

| Reaction Time (h) | % ee of | | % Conv. | E |
|---|---|---|---|---|
| | R-acid | S-Ester | | |
| Iodide Salt | | | | |
| 24 | 91.0 | 13.1 | 12.6 | 24.0 |
| 48 | 91.6 | 28.0 | 23.4 | 29.9 |
| 120 | 86.6 | 69.1 | 44.4 | 28.8 |
| 168 | 81.4 | 82.4 | 50.3 | 24.8 |
| Methyl Sulfate Salt | | | | |
| 24 | 82.5 | 14.1 | 14.6 | 11.9 |
| 48 | 81.6 | 27.4 | 25.1 | 12.8 |
| 120 | 83.6 | 63.3 | 43.1 | 21.4 |
| 168 | 80.4 | 75.3 | 48.4 | 20.7 |

The somewhat higher ee and better E values of the iodide salts appear to be related to the higher initial purity of the choline ester in the iodide salt, rather than an effect of the salt per se.

In a larger scale reaction, 3 L of stationary phase *Beauveria bassiana* ATCC 44860 hydrolyzed racemic Ketoprofen choline ester methylsulfate salt at an initial rate of 14.3 g/L/day. After 4 days the remaining S-ester was over 90% ee. Because both the R-acid or S-acid can readily be crystallized (without the use of resolving agents, i.e., chiral amines) to over 98% ee if the starting material is of 90% ee or greater, the level of enrichment obtained with this hydrolysis represents a direct route to optically pure R- and S-ketoprofen.

Three hundred mL of stationary phase *Beauveria bassiana* ATCC 44860 were inoculated into 3 L of Brain Heart Infusion medium supplemented with 25 g of soybean flour and 100 mL of olive oil. The culture was incubated at 25° C. and buffered at pH 6.1 with stirring for 7 days at which time 160 g of racemic ketoprofen choline ester methylsulfate salt was added. At the indicated times samples were taken and analyzed for R-acid and S-ester by chiral HPLC. The progress of the reaction as a function of time is shown in Table 2.

TABLE 2

| Reaction Time (days) | % ee of R-acid | % ee of S-Ester | % Conv. | E | R-acid g/L/day |
|---|---|---|---|---|---|
| 0.9 | 58.0 | 56.7 | 44.0 | 11.0 | 14.3 |
| 2.0 | 67.0 | 75.4 | 50.6 | 15.2 | 7.6 |
| 3.0 | 65.1* | 85.5 | 53.5 | 18.9 | 5.3 |
| 4.0 | 63.6* | 90.8 | 55.6 | 19.3 | 4.2 |
| 7.0 | 62.0* | 95.8 | 59.7 | 17.2 | 2.5 |

*We hypothesize that because of the high concentration, the acid was crystallizing out during the fermentation; the analysis was based on ketoprofen in solution at that point in time.

Another example illustrating that hyphae of Beauveria bassiana ATCC 44860 stereospecifically hydrolyze the R-ester of ketoprofen choline ester is shown in Table 3. In this experiment cells from a 60 mL stationary phase culture were harvested and suspended in 25 mL of 2X Brain Heart Infusion Medium containing 5 g of the iodide salt of the choline ester. After 33.9% conversion, there was 93.6% ee of the R-acid. Particularly noteworthy is the E value of 54.7 on day 6.

TABLE 3

| Reaction Time (days) | % ee of R-acid | % ee of S-Ester | % Conversion | E | R-acid g/L/day |
|---|---|---|---|---|---|
| 1 | 56.6 | 1.1 | 1.7 | 3.6 | 1.9 |
| 2 | 92.2 | 6.4 | 6.5 | 26.2 | 3.6 |
| 3 | 94.9 | 12.5 | 11.6 | 43.3 | 4.3 |
| 6 | 95.4 | 25.4 | 21.0 | 54.7 | 3.9 |
| 7 | 93.7 | 28.7 | 23.5 | 40.7 | 3.2 |
| 8 | 94.6 | 31.8 | 25.2 | 48.7 | 3.5 |
| 14 | 93.6 | 48.0 | 33.9 | 48.7 | 2.7 |

An R-specific ketoprofen ester hydrolase is only one of many enzymes that are found in Beauveria. It seemed likely that the fungus not only contained a very stereospecific ester hydrolase but also less selective enzymes and that the selectivity observed with the intact organism may be an average of several different enzymatic activities. Data in Table 4 suggest that this is the case.

Intact Beauveria cells, a cell pellet obtained by centrifugation of a cellular homogenate, and a crude extract (the supernatant fraction obtained after centrifugation of a cellular homogenate) were compared for ketoprofen choline ester hydrolysis activity. The results are shown in Table 4. Highest E values were associated with the intact cells and cell pellet. Other experiments showed that the enzyme was not extracellular, i.e., secreted into the medium. The low E values obtained with the crude extract suggest that Beauveria contains one or more cytoplasmic enzymes of low specificity for the R-ester.

A one-mL (final volume) reaction mixture contained ketoprofen choline ester (6 mg), NaPi buffer (200 mM, pH 6.5), and 150 mg of whole cells or pellet, or 300 µL cell crude extract. The reaction was carried out at 30° C. in a shaker with a reciprocal speed of 169 rpm. Routine assays of the enzyme were performed by using p-nitrophenyl ketoprofen as a substrate at 30° C.

TABLE 4

| Incubation Time (hour) | Experiment | ee of R-acid (%) | ee of S-ester (%) | % Conv. | E |
|---|---|---|---|---|---|
| 24 | whole cell | 75.92 | 44.95 | 37.19 | 11.32 |
|  | pellet | 73.63 | 50.23 | 40.55 | 10.77 |
|  | crude extract | 51.46 | 11.99 | 18.90 | 3.50 |
| 48 | whole cell | 72.46 | 77.32 | 51.62 | 14.41 |
|  | pellet | 67.50 | 52.46 | 52.46 | 11.28 |
|  | crude extract | 43.95 | 18.57 | 29.70 | 3.06 |
| 72 | whole cell | 67.12 | 77.27 | 53.51 | 11.61 |
|  | pellet | 62.13 | 74.25 | 56.05 | 10.04 |
|  | crude extract | 44.77 | 24.86 | 35.70 | 3.31 |

Partial purification of the R-specific ester hydrolase enzyme can be accomplished as described below. This preparation shows high selectivity for the R-ester.

The purification of the enzyme was carried out at room temperature unless it is otherwise indicated.

Step 1. Extraction of the enzyme

Approximately 120 g of frozen cells of *Beauveria bassiana* were thawed and extracted twice with 250 mL of phosphate buffer (50 mM, pH 6.5 and containing 150 mM KCl) using a Bead Beater (BioSpec Products, Bartlesville, OKLA.). The cell extract was filtered through a sintered glass filter with suction; the filtrate was then centrifuged at 16000 rpm for 40 minutes to recover the enzyme in the supernatant fraction.

Step 2. Dialysis. The enzyme sample was dialyzed against 6 L of phosphate buffer (50 mM, pH 6.5) and one change of the buffer for 16 hours at 4° C. The dialysis of the enzyme sample resulted in a heavy precipitate, which was removed and discarded.

Step 3. DEAE-Spherodex column chromatography.

The clear, dialyzed enzyme sample was applied to a DEAE-Spherodex column (5×8 cm) which was equilibrated with the phosphate buffer. Most of the enzymic activity was recovered in the flow-through fraction, which was then concentrated by an Amicon Diaflo ultrafiltration unit fitted with a YM 10 membrane (Beverly, MA) to about 20 mL.

Step 4. Ultrogel AcA 44 column chromatography.

The concentrated enzyme sample from the previous step was loaded on an Ultrogel AcA 44 column (2.5×90 cm). The enzyme was eluted with sodium acetate buffer (50 mM, pH 6 and 0.02% sodium azide) at a flow rate of 14 mL per hour. Those fractions rich in enzymic activity were pooled and stored at −20° C.

A summary of the enzyme purification is given in Table 5.

TABLE 5

| Procedure | Volume (mL) | Units/mL | Total Units | Protein (mg/mL) | Units/mg Protein | Yield % |
|---|---|---|---|---|---|---|
| 1. Extraction | 529 | 243 | 128547 | 3.6 | 67.1 | 100 |
| 2. Dialysis | 600 | 154 | 92400 | 1.6 | 94.9 | 72 |

TABLE 5-continued

| Procedure | Volume (mL) | Units/ mL | Total Units | Protein (mg/mL) | Units/ mg Protein | Yield % |
|---|---|---|---|---|---|---|
| 3. DEAE-Spherodex column | 610 | 142 | 86620 | 1.1 | 129.3 | 67 |
| 4. Ultrogel AcA 44 column | 110 | 517 | 56870 | 0.7 | 729.2 | 44 |

In subsequent experiments it has been found that by deleting the KCl in step 1, the dialysis (step 2) can be eliminated. It has been further found that the elimination of step 4 provides an enzyme preparation of roughly comparable utility in that the ee and E values are not significantly poorer than those of the purified enzyme after step 4.

The effect of pH on esterase activity was examined initially using 5 mg of ketoprofen choline ester in 800 μL of 200 mM NaPi buffer with 200 μL of a 7,152 mg/mL enzyme solution. The results from pH 8.0 to 6.0 are shown in Table 6. The medium was then modified slightly (10 mg ester, 920 μL buffer, 80 μL of 24 mg/mL or 19.038 units/mL enzyme solution at 30° C.) and the range from pH 4.5 to 6.0 was examined. The results are shown in Table 7. The optimum appears to be pH 5.5, where E values of over 100 were obtained.

TABLE 6

| Incubation Time (hour) | pH | ee of R-acid (%) | ee of S-ester (%) | % Conv. | E |
|---|---|---|---|---|---|
| 2 | 6.0 | 94.08 | 30.36 | 24.40 | 44.09 |
|  | 6.5 | 93.88 | 31.54 | 25.15 | 43.11 |
|  | 7.0 | 91.64 | 34.42 | 27.30 | 32.08 |
|  | 7.5 | 87.26 | 34.62 | 28.40 | 20.59 |
|  | 8.0 | 78.68 | 30.35 | 27.84 | 11.24 |
| 6 | 6.0 | 92.04 | 92.20 | 50.04 | 79.83 |
|  | 6.5 | 89.06 | 94.20 | 51.40 | 61.71 |
|  | 7.0 | 85.68 | 95.04 | 52.59 | 47.89 |
|  | 7.5 | 82.12 | 93.70 | 53.29 | 35.21 |
|  | 8.0 | 75.12 | 92.94 | 55.30 | 23.35 |
| 20 | 6.0 | 88.64 | 88.08 | 49.84 | 51.80 |
|  | 6.5 | 83.40 | 89.06 | 51.64 | 32.80 |
|  | 7.0 | 74.50 | 90.26 | 54.78 | 20.75 |
|  | 7.5 | 62.44 | 82.22 | 56.84 | 10.69 |
|  | 8.0 | 43.48 | 70.64 | 61.90 | 5.09 |

TABLE 7

| Incubation Time (hour) | pH | ee of R-acid (%) | ee of S-ester (%) | % Conv. | E |
|---|---|---|---|---|---|
| 1 | 4.5 | 96.48 | 8.36 | 7.97 | 60.62 |
|  | 5.0 | 96.04 | 11.46 | 10.66 | 55.42 |
|  | 5.5 | 97.50 | 15.66 | 13.84 | 92.12 |
|  | 6.0 | 96.46 | 20.74 | 17.70 | 67.98 |
| 2 | 4.5 | 97.16 | 16.00 | 14.14 | 81.22 |
|  | 5.0 | 97.42 | 20.36 | 17.29 | 93.39 |
|  | 5.5 | 97.68 | 29.54 | 23.22 | 113.74 |
|  | 6.0 | 97.46 | 36.54 | 27.27 | 111.24 |
| 4 | 4.5 | 94.42 | 28.42 | 23.14 | 45.98 |
|  | 5.0 | — | — | 31.46 | — |
|  | 5.5 | 96.90 | 59.08 | 37.88 | 115.96 |
|  | 6.0 | 96.20 | 62.24 | 39.28 | 97.93 |
| 7 | 4.5 | 95.90 | 41.22 | 30.06 | 71.69 |
|  | 5.0 | 96.10 | 51.00 | 34.67 | 83.67 |
|  | 5.5 | 96.18 | 67.72 | 41.32 | 104.58 |
|  | 6.0 | 95.84 | 78.40 | 45.00 | 112.74 |

Other experiments with purified enzyme at pH 6.0 paralleled those observed earlier with the whole Beauveria cells. Once again the iodide salt gave rise to higher E values but at a slightly reduced conversion rate, probably due to the higher initial purity of the iodide salt ester. A one-mL reaction mixture contained substrate (10 or 50 mg), sodium phosphate buffer (200 mM, pH 6), 0.87 mL; concentrated *Beauveria bassiana* enzyme (12000 U/mL and protein concentration of 19.641 mg/mL), 0.13 mL. Reaction was carried out at room temperature (approximately 21° C.) with stirring. The results are shown in Table 8:

TABLE 8

| Substrate | Incubation Time (h) | Concentration (mg/ml) | % ee R | % ee S | % Conv. | E |
|---|---|---|---|---|---|---|
| Ketoprofen choline ester methysulfate salt | 2 | 10 | 88.95 | 9.94 | 10.05 | 18.86 |
|  | 2 | 50 | 87.28 | 4.21 | 4.60 | 15.35 |
|  | 7 | 10 | 88.20 | 33.10 | 27.29 | 22.02 |
|  | 7 | 50 | 88.80 | 8.58 | 8.81 | 18.36 |
| Ketoprofen choline ester iodide salt | 2 | 10 | 96.35 | 8.60 | 8.19 | 58.56 |
|  | 2 | 50 | 95.20 | 2.14 | 2.20 | 41.54 |
|  | 7 | 10 | 96.32 | 33.22 | 25.64 | 73.83 |
|  | 7 | 50 | 95.04 | 5.46 | 5.43 | 41.51 |

The partially purified enzyme preparation was used to demonstrate that the acid product of the reaction was inhibitory (approximately 45% inhibition at 40 mM acid), while the choline product did not appear inhibitory. From the activity of the preparation at different concentrations of substrate an estimated $k_m$ of 4.96 mM was obtained.

Although the enzyme hydrolyzes the water-soluble choline ester, it appears that the enzyme might be a lipase. This conclusion is based on the fact that the enzyme is more active with p-nitrophenyl palmitate than with p-nitrophenyl acetate (see Table 9) and on the observation that the enzyme preparation readily hydrolyzes olive oil. The enzyme, although sensitive to PMSF (phenylmethylsulfonylfluoride), appears not to be a protease because the preparation does not hydrolyze azocasein or N-succinyl-ala-ala-pro-phe-p-nitroaniline, another protease substrate. The sensitivity of PMSF suggest that a serine is part of the active site of this ester hydrolase.

TABLE 9

| Substrate | Enzymic activity (n mole substrate hydrolyzed/min/mL enzyme) |
| --- | --- |
| p-nitrophenyl Ketoprofen | 11 |
| p-nitrophenyl acetate | 215 |
| p-nitrophenyl palmitate | 7496 |

Insertion of a chromatofocusing step following DEAE-Spherodex chromatography (see Table 5) and subsequent size exclusion chromatography and reverse phase HPLC allowed purification of the enzyme to homogeneity. Chromatofocusing was carried out with PBE™94 resin (Pharmacia Fine Chemicals, Sweden) and the R-specific ester hydrolase eluted between pH 7.15 and 6.54.

The estimated molecular weight of the enzyme from a reduced SDS polyacrylamide gel was approximately 17,500 daltons. Whether the enzyme is composed of several subunits is unknown. Thus, 17,500 daltons may represent a monomeric subunit and the enzyme may have a molecular weight that is some multiple of 17,500. The purified enzyme monomer did not react with periodate-Schiff's base, indicating that this enzyme is not a glycoprotein. The amino acid analysis of the purified enzyme monomer is shown in Table 10. The molecular weight was estimated to be approximately 17,800 daltons exclusive of tryptophan and cysteine.

TABLE 10

| Aminoacid | Number of Residue |
| --- | --- |
| Asp* | 14 |
| Glu* | 10 |
| Ser | 10 |
| Gly | 16 |
| His | 2 |
| Arg | 4 |
| Thr | 12 |
| Ala | 21 |
| Pro | 14 |
| Tyr | 5 |
| Val | 14 |
| Met | 8 |
| Cys+ | ? |
| Ile | 8 |
| Leu | 12 |
| Phe | 8 |
| Trp‡ | ? |
| Lys | 12 |
| TOTAL | 170 |

TABLE 10-continued

| Aminoacid | Number of Residue |
| --- | --- |

$M_r = 17848$
*Asn and Gln are converted to their respective acid derivatives Asp and Glu during hydrolysis.
+Cys is partially destroyed during hydrolysis and is therefore not included in the above data, even if present.
‡Trp is destroyed during hydrolysis and would most likely not be detected if present in the protein.

The N-terminal and two internal fragments of the enzyme were sequenced. The sequence of the N-terminus was determined to be:

Ala-Pro-Asp-W-Ile-Ile-Gln-Gly-Leu-Ser-Arg-Ala-X-Asp-Gly-Gln-Asp  (SEQ ID NO:1)

where W and X are unidentified aminoacids. Sequences of internal fragments obtained by digestion with the endopeptidase, lysC, and subsequent purification of the fragments by reverse phase HPLC prior to sequencing were Phe-Ala-Ile-Asn-Asn-Gln-Leu-Thr-Ala-Pro-Thr-Ala-Y-Thr-Tyr-Val-Val-Lys  (SEQ ID NO:2)

and

Leu-Ile-Ala-Tyr-Pro-Ala-Tyr-Asn-Asp-Glu-Ile (?)-Ala-Ala-Gly-Asn-Val-Pro-Asp-Lys-Ile(?)-Phe(?)-His  (SEQ ID NO:3)

The "Y" indicates that the amino acid at this position has not been identified while the (?) indicates that the assignment is not certain.

The addition of low levels of an oil (about 1 part oil in 50 to 100 parts of medium) such as olive oil, to the BHI medium stimulates conversion and enhances selectivity.

A preferred medium for growing Beauveria is BHI. Beauveria will grow and will enantioselectively hydrolyze ketoprofen choline ester in many other media known to persons of skill in the art, but the results are not as good as with BHI. A temperature between 0° and 45° C. and a pH between 3.5 and 9 is maintained during the growth of the microorganisms. Preferably the microorganisms are grown at a temperature between 20° and 37° C. and at a pH between 5 and 9.

A less expensive medium that produces acceptable results is: ammonium nitrate (6 g/L); potassium chloride (1 g/L); magnesium sulfate heptahydrate (1 g/L); dibasic potassium phosphate (2 g/L); ferrous sulfate heptahydrate (0.2 g/L); soy flour (1 g/L); soy oil (6.7 mL/L) and glucose (40 g/L). The fermentation in this medium is optionally maintained at pH 6.0 to 6.5 at 25° C.

The aerobic conditions required during the growth of the micro-organisms can be provided according to any of the well-established procedures, provided that the supply of oxygen is sufficient to meet the metabolic requirement of the micro-organisms. This is most conveniently achieved by supplying oxygen, suitably in the form of air and optionally at the same time shaking or stirring the reaction liquid. During the hydrolysis of the ester the micro-organisms might be in a growing stage or might be preserved in any system (medium or buffer) preventing degradation of enzymes.

During the hydrolysis of the ester, an ordinary culture medium may be used containing an assimilable carbon source when required (for example glucose, sucrose, etc.), a nitrogen source when required (for example ammonium sulphate, potassium nitrate, sodium nitrate, ammonium nitrate, etc.), with an agent for an organic nutrient source when required (for example yeast extract, malt extract, peptone, meat extract, etc.) and an inorganic nutrient source when required (for example phosphate, magnesium, potassium, zinc, iron and other metals in trace amounts).

The microorganisms can be kept in the non-growing stage, for example, by exclusion of the assimilable carbon source or by exclusion of the nitrogen source. A temperature between 0° and 45° C. and a pH between 3.5 and 9 is maintained during this stage.

The ketoprofen produced by the microorganisms or substances derived therefrom, as mentioned above, can be recovered and purified according to any of the procedures known per se for such products and described, for example, in U.S. pat No. 5,108,916. A typical work-up would be as follows: When approximately 40% acid is produced, the reaction is stopped by filtering or centrifuging the Beauveria cells and decanting the supernatant. The aqueous filtrate or supernatant is acidified to pH 1.5 with HCl and extracted into methyl t-butylether. The ether can be evaporated and the ketoprofen recrystallized if desired. The recovery can be monitored by TLC on silica plates using 95:5 $CHCl_3$: $CH_3OH$ and iodine vapor development, as well as by HPLC.

Microorganisms that have obtained the ability for selective hydrolysis of ketoprofen water-soluble esters through the introduction of genetic material from *Beauveria bassiana* or related Beauveria species are also encompassed within the invention. The introduction of genetic material can be accomplished by transferring the cloned gene encoding the Beauveria ester hydrolase to another organism by methods well-known in the art. Suitable host microorganisms are, for example, members of the genera Saccharomyces, Kluyveromyces, Aspergillus, Escherichia, Pseudomonas and Streptomyces. The ester hydrolases, and even the microorganisms themselves, can be immobilized and used according to methods well known in the art. Suitable methods for immobilization are described in U.S. pat. Nos. 4,436,813 and 4,650,755 and copending U.S. application Ser. No. 087/908493 the disclosures of which are incorporated herein by reference.

A particularly advantageous device and method for removing the inhibitory product and thereby efficiently driving the reaction is described in U.S. pat. No. 5,077,217 (Matson et al.) the disclosure of which is incorporated herein by reference. Using the method of Matson as described in example 6.2.1 (column 43, line 36), an initial reaction mixture of partially purified Beauveria ester hydrolase (180,000) units and 10 g of racemic ketoprofen choline ester methylsulfate salt in 280 mL of 50 mM sodium phosphate buffer at pH 5.3 was run through an extractive membrane reactor at room temperature while the product was extracted into 450 mL of toluene. The toluene was reextracted with 1.8 L of 0.1M aqueous $Na_2CO_3$ at pH 10.45. Additional substrate in buffer was added as shown in the volume and substrate columns in Table 11. At 91 hours, the yield of recovered R-acid was 94% of the theoretical value (i.e., of the amount formed during the hydrolysis reaction).

TABLE 11

| Time (h) | Vol. (mL) | Substrate (g) | % e.e. R-acid | % e.e. S-ester | % conv. | E | R-acid g/L | Rate g/L/day |
|---|---|---|---|---|---|---|---|---|
| 2.5 | 280 | 10 | 93.46 | — | — | — | — | — |
| 5 | 300 | 30 | 93.32 | — | — | — | — | — |
| 18 | 350 | 30 | 96.44 | 33.84 | 26.0 | 76.8 | 12.48 | 16.64 |
| 26 | 350 | 30 | 95.54 | — | — | — | — | — |
| 29 | 400 | 60 | 95.86 | — | — | — | — | — |
| 45 | 400 | 60 | 95.94 | 36.72 | 27.7 | 69.2 | 23.27 | 9.59 |
| 50 | 400 | 60 | 95.90 | — | — | — | — | — |
| 53 | 450 | 90 | 96.56 | 25.60 | 21.0 | 73.4 | — | — |
| 68 | 450 | 90 | 95.92 | — | — | — | — | — |
| 75 | 450 | 90 | 94.86 | — | — | — | — | — |
| 91 | 450 | 90 | 94.66 | 29.70 | 23.90 | 48.8 | 26.77 | 1.83 |
| 187 | 450 | 90 | 85.76 | 39.50 | 31.53 | 31.5 | 31.5 | 2.14 |

While the invention has been particularly shown and described with reference to preferred embodiments thereof, it will be understood by those skilled in the art that other changes in form and details may be made therein without departing from the spirit and scope of the invention.

We claim:

1. A process for preferentially hydrolyzing R-ketoprofen choline ester in the presence of S-ketoprofen choline ester comprising contacting an aqueous solution of a mixture of ketoprofen choline ester enantiomers with an organism of the species *Beauveria bassiana* at pH 4.0 to pH 8.0 and at a temperature of 10° to 40° C., and recovering R-ketoprofen.

2. A process according to claim 1 wherein said *Beauveria bassiana* is selected from strains ATCC 44860, 38657 and 7159.

3. A process according to claim 2 wherein said *Beauveria bassiana* is strain ATCC 44860.

4. A process according to claim 1 wherein said temperature is about 25° C. and said pH is maintained at 5.5 to 6.5.

5. A process according to claim 1 wherein said aqueous solution additionally contains a source of nutrients for said *Beauveria bassiana*.

6. A process for producing R-ketoprofen comprising contacting a choline ester of R-ketoprofen with an organism of the species *Beauveria bassiana* and recovering the R-ketoprofen.

7. A process according to claim 6 wherein said choline ester of R-ketoprofen is contacted with said *Beauveria bassiana* at pH 5.5 to 6.5 and at about 25° C.

8. A process according to claim 6 wherein said *Beauveria bassiana* is selected from ATCC strains 44860, 38657 and 7159.

9. A process for obtaining R-ketoprofen from racemic ketoprofen comprising:
   (a) reacting racemic ketoprofen with a suitable precursor to produce a choline ester of racemic ketoprofen;
   (b) treating said choline ester of racemic ketoprofen in water with a fungus of the species *Beauveria bassiana* to produce preferentially R-ketoprofen in the presence of ketoprofen choline ester which has become enriched in the S-enantiomer; and
   (c) isolating said R-ketoprofen from said ketoprofen choline ester.

10. A process for obtaining R-ketoprofen from racemic ketoprofen comprising:
   (a) reacting racemic ketoprofen with an activating agent to provide an activated ketoprofen;
   (b) reacting said activated ketoprofen with choline to produce a choline ester of racemic ketoprofen;
   (c) treating said choline ester of racemic ketoprofen in water with a fungus of the species *Beauveria bassiana* to produce preferentially R-ketoprofen in the presence of S-enriched ketoprofen choline ester; and
   (d) isolating said R-ketoprofen from said S-enriched ketoprofen choline ester.

11. A process for obtaining R-ketoprofen from racemic ketoprofen comprising:
   (a) reacting racemic ketoprofen with an activating agent to provide an activated ketoprofen;
   (b) reacting said activated ketoprofen with choline to produce a choline ester of racemic ketoprofen;
   (c) treating said choline ester of racemic ketoprofen in water with an ester hydrolase from a fungus of the species *Beauveria bassiana* to produce preferentially R-ketoprofen in the presence of S-enriched ketoprofen choline ester; and
   (d) isolating said R-ketoprofen from said S-enriched ketoprofen choline ester.

12. A process for preferentially hydrolyzing R-ketoprofen choline ester in the presence of S-ketoprofen choline ester, comprising contacting an aqueous solution of a mixture of ketoprofen choline ester enantiomers with an R-ketooprofen choline ester hydrolase from *Beauveria bassiana* at pH 4.0 to pH 8.0 and at a temperature of 10° to 40° C., and recovering R-ketoprofen.

13. A process according to claim 12 wherein said ester hydrolase has an approximate molecular weight of 17,800 dalton on an SDS polyacrylamide gel, an N-terminal sequence of Ala-Pro-Asp-W-Ile-Ile-Gln-Gly-Leu-Ser-Arg-Ala-X-Asp-Gly-Gln-Asp-(SEO ID NO:1), and internal sequences of -Phe-Ala-Ile-Asn-Asn-Gln-Leu-Thr-Ala-Pro-Thr-Ala-Y-Thr-Tyr-Val-Val-Lys-(SEQ ID NO:2) and -Leu-Ile-Ala-Tyr-Pro-Ala-Tyr-Asn-Asp-Glu-Z-Ala-Ala-Gly-Asn-Val-Pro-Asp-Lys-(SEQ ID NO:3), where W, X, Y and Z represent an amino acid.

14. A process for obtaining S-ketoprofen from racemic ketoprofen comprising:
   (a) reacting racemic ketoprofen with an activating agent to provide an activated ketoprofen;
   (b) reacting said activated ketoprofen with choline to provide a choline ester of racemic ketoprofen.
   (c) treating said choline ester of racemic ketoprofen in water with a fungus of the species *Beauveria bassiana* to produce a mixture consisting essentially of S-enriched ketoprofen choline ester and R-ketoprofen;
   (d) separating said R-ketoprofen from said S-enriched ketoprofen choline ester; and
   (e) hydrolyzing said S-enriched ketoprofen choline ester.

* * * * *